United States Patent [19]

Hornykiewicz et al.

[11] Patent Number: 4,645,770

[45] Date of Patent: Feb. 24, 1987

[54] AGENT FOR TREATING PARKINSON'S DISEASE OR PARKINSONISM

[75] Inventors: Oleh Hornykiewicz, Vienna, Austria; Dieter Hinzen, Zornheim; Günter Schingnitz, Bad Kreuznach, both of Fed. Rep. of Germany

[73] Assignee: Boehringer Ingelheim KG, Ingelheim am Rhein, Fed. Rep. of Germany

[21] Appl. No.: 825,519

[22] Filed: Feb. 3, 1986

[30] Foreign Application Priority Data

Feb. 6, 1985 [DE] Fed. Rep. of Germany ....... 3503963
Mar. 6, 1985 [DE] Fed. Rep. of Germany ....... 3507861

[51] Int. Cl.$^4$ .............................................. A61K 31/55
[52] U.S. Cl. ..................................................... 514/212
[58] Field of Search ......................................... 514/212

Primary Examiner—Stanley J. Friedman
Attorney, Agent, or Firm—David E. Frankhouser; Alan R. Stempel

[57] ABSTRACT

The invention describes the use of 2-amino-6-allyl-5,6,7,8-tetrahydro-4H-thiazolo[4,5-d]azepine and the acid addition salts thereof for the treatment of Parkinson's disease or Parkinsonism.

1 Claim, No Drawings

AGENT FOR TREATING PARKINSON'S DISEASE OR PARKINSONISM

BACKGROUND OF THE INVENTION

1. Field of the Invention

The present invention relates to a method of treating Parkinson's disease or Parkinsonism which comprises administering 2-amino-6-allyl-5,6,7,8-tetrahydro-4H-thiazolo [4,5-d]azepine or an acid addition salt thereof.

2. Description of the Prior Art

Belgian Pat. Nos. 684 515 and 771 330 describe, inter alia, thiazole and oxazole derivatives of general formula

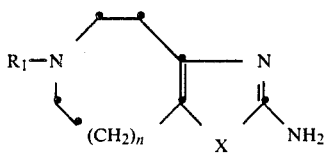

wherein $R_1$ represents a hydrogen atom, an alkyl group with 1 to 4 carbon atoms optionally substituted by hydroxyl group, a benzyl group optionally substituted by a halogen atom or by a methyl or methoxy group, or an allyl group, n represents the number 2 or also the number 1 if X represents a sulphur atom and X represents an oxygen or sulphur atom, and the physiologically acceptable acid addition salts thereof with inorganic or organic acids.

It is known from Belgian Pat. Nos. 684 415 and 771 330 that the compounds of general formula I and the physiologically acceptable acid addition salts thereof have valuable pharmacological properties. Thus, the compounds described in Belgian Pat. No. 684 415 have, in particular, an analgesic, sedative, antitussive, antipyretic and antiphlogistic activity and the compounds described in Belgian Pat. No. 771 330, depending on their substitution, have a hypotensive, sedative, antitussive and/or antiphlogistic activity.

It is also apparent from the above-mentioned patent specifications that the thiazole derivatives of general formula I
wherein $R_1$ represents an alkyl group with 1 to 4 carbon atoms or an allyl group, n represents the number 2 and X represents a sulphur atom, have a hypotensive activity in particular and the oxazole derivatives of general formula I wherein $R_1$ represents a hydrogen atom, an alkyl group with 1 to 4 carbon atoms optionally substituted by a hydroxy group, or an allyl group, n represents the number 2 and X represents an oxygen atom, have antitussive properties in particular.

It is known from No. EP-A1-0 005 732 that the compounds of general formula I above wherein n represents the number 2 also have an anti-angina activity.

It is also known from U.S. Pat. No. 4,400,378 that the compounds of general formula I also have an anti-glaucoma activity.

According to the existing scientific publications, the compound 2-amino-6-allyl-5,6,7,8-tetrahydro-4H-thiazole-[4,5-d]azepine dihydrochloride (B-HT 920) has been regarded as an agonist with a selective effect on presynaptic dopaminergic receptors (e.g. Anden et al., Acta Pharmacol. et Toxicol., 52, 51–56 (1983) and J. Neural Transmission 59, 129–137 (1983)).

DESCRIPTION OF THE INVENTION

The present invention is based on the surprising discovery that B-HT 920 also develops an agonistic activity on denervated or degenerate postsynaptic dopaminergic structures of the brain. This discovery marks out the compound particularly for the treatment of Parkinson's disease or Parkinsonism. These diseases are caused by the degeneration of dopaminergic neurons in the brain. The chemical messenger dopamine is therefore not released in sufficient quantities during neuron acivity, resulting in the appearance of the Parkinson's symptoms.

Nilsson & Carlsson (TIPS Reviews, Elsevier Biomedical Press, August 1982, p 322 ff.) state that the most advantageous substances for treating Parkinsonism or Parkinson's disease are those which have a specific agonistic effect on the postsynaptic dopaminergic neurons. Goodale et al., Science 210, 1141–1143 (1980) also write: ". . . a compound which primarily activates the postsynaptic receptors would be indicated in diseases of reduced dopamine release, such as Parkinson's disease".

The first object of the invention is a method of treating Parkinson's disease or Parkinsonism, characterized in that the patient is given a sufficient quantity of the compound 2-amino-6-allyl-5,6,7,8-tetrahydro-4H-thiazolo[4,5-d]azepine (hereinafter referred to as Compound A) or one of the acid addition salts thereof, in order to alleviate or remove the symptoms of the disease.

A further object of the invention is the use of compound A or the acid addition salts thereof for preparing pharmaceutical compositions suitable for the treatment of Parkinson's disease or Parkinsonism.

For the treatment of Parkinson's disease or Parkinsonism, the compounds A and the suitable acid addition salts thereof may be incorporated in the usual galenic preparations for oral, parenteral, rectal or transdermal application.

The single dose for oral administration in man is normally between 2.5 mcg and 350 mcg, preferably between 100 mcg and 250 mcg; in the case of several administrations (e.g. 3 times a day) the daily doses may range from 15–900 mcg, preferably from 30–750 mcg. The parenteral and rectal doses may be of the same order of magnitude as the quantities of substance to be administered by oral route.

German Patent application No. P 35 03 963.9 describes an investigation of the anti-Parkinson's effect of B-HT 920, the hydrochloride of Compound A. The investigation was carried out on rats.

The following methods of investigation were used.

(A) Spontaneous motor activity in the "naive" rat

Two aspects of motor function were recorded with a known "Opto-Varimex 3":

(a) "ambulatory" movements in the first 5 minutes after s.c. injection of B-HT 920; this phase of locomotor function corresponds to the so-called "exploratory activity" of rats in a new environment;

(b) "non-ambulatory" movements which are made up essentially of stereotypical movements, which began to be recorded 45 minutes after the animals had been put into the recording cage (and 55 minutes after s.c. injection).

Test results

Exploratory activity and stereotypical movements

The following doses of B-HT 920 were tested: 0.02, 0.2, 2.0 mg/kg s.c.. As a comparison apomorphine was tested in a dosage of 0.1 mg/kg s.c.

The following Table contains the values found:

TABLE 1

| Dose mg/kg | Contacts broken (exploratory activity/5 min.) | Stereotypical movements Movements/15 min. |
|---|---|---|
| B-HT 920 | | |
| 0 (control) | 680 | 370 |
| 0.02 | 380 | n.t. |
| 0.2 | 150 | 370 |
| 2.0 | 130 | 310 |
| 4.0 | n.t. | 340 |
| apomorphine | | |
| 0.1 | 150 | n.t. |
| 4.0 | n.t. | 650 | n.t. = not tested

The inhibitory effect of B-HT 920 on the exploratory activity was therefore almost maximum at a dosage of 0.2 mg/kg and was comparable with a corresponding effect of 0.1 mg/kg of apomorphine (which also reduced the number of breakings of the contacts to 150 per 5 minutes).

With regard to stereotypical movements, B-HT 920 did not lead to an increase in the number of stereotypical movements at any of the doses tested.

By contrast with B-HT 920, 4.0 mg/kg of apomorphine led to an increase in the number of stereotypical movements to a level of 650.

(B) Ipsilateral rotation in the ibotenic acid model in the rat

By analogy with the corresponding kainic acid model according to Schwarcz et al (Brain Res. 170 (1979) 485–495). This model is based on the fact that unilateral intra-striatal (stereotactical) injection of the neurotoxin ibotenic acid destroys the striatum cells on which there are also postsynaptic dopamine (DA) receptors (cf. Schwarcz et al., Exper. Brain Res. 37 (1979) 199–216), so that post-synaptic DA agonists can only act on the corresponding DA receptors on the intact side and therefore cause movements of rotation of the animal to the side of the damaged striatum.

Test results

The following doses of B-HT 920 were tested: 0.2, 0.5, 1.0 and 2.0 mg/kg s.c.. As a comparison, apomorphine was tested in a dosage of 0.1 mg/kg s.c. The following Table contains the values found:

TABLE 2

| Active substance | Ipsilateral rotations/duration of activity up to 3 hours (apomorphine) up to 6 hours (B-HT 920) Dosage mg/kg | | | | |
|---|---|---|---|---|---|
| | 0.2 | 0.5 | 1.0 | 2.0 | 10.0 |
| B-HT 920 | 37 | 54 | 102 | 96 | — |
| apomorphine | — | 265 | 436 | — | 880 |

A comparison between apomorphine and B-HT 920 shows that B-HT 920 has only about one eighth of the post-synaptic DA-agonistic activity of apomorphine on the normally sensitive DA receptor, i.e. it has only a weak activity in this respect.

(C) Contralateral rotation on the 6-OHDA model according to Ungestedt (Acta physiol scand. suppl 367 (1971) 69 ff; Europ. J. Pharmacol. 98 (1984) 165–176). This model is based on the fact that stereotactical unilateral injection of the neurotoxin 6-OHDA destroys the nigrostriatal DA path on one side so that the post-synaptic DA receptors in the ipsilateral striatum are robbed of their DA innervation, i.e. they are denervated, and consequently have a (denervation) hypersensitivity. In this model, DA-agonists with a post-synaptic activity cause rotational movements to the contralateral side even at fairly low doses by a preferential activity on the hypersensitive DA receptors.

Test results

The following doses of B-HT 920 were tested: 0.02, 0.05, 0.5, 1.0 mg/kg. As a comparion, apomorphine was tested in a dosage of 0.05 mg/kg s.c. The following Table contains the values found:

| Dosage mg/kg | Contralateral rotations up to 6 hours | |
|---|---|---|
| | B-HT 920 | apomorphine |
| 0.02 | 168 | — |
| 0.05 | 582 | 557 |
| 0.5 | 1282 | — |
| 1.0 | 1442 | — |

Compared with B-HT 920, 0.05 mg/kg of apomorphine resulted in 557 contralateral rotations per period of activity. It can therefore be concluded that, by contrast with its weak effect on normal DA receptors, B-HT 920 has an exceptionally strong activity on denervated receptors.

The discovery of the neurotoxin 1-methyl-4-phenyl-1,2,3,6-tetrahydropyridine (MPTP) 18 months ago (Langston et al., Science 219, 979 (1983)) has provided a further animal model for Parkinson's disease.

The irreversible neurological syndrome triggered in monkeys and humans by MPTP largely resembles idiopathic Parkinson's disease in its clinical, pathological, biochemical and pharmacological features (Markey et al., Nature 311, 464 (1984)). The reason for this strong similarity is the fact that MPTP selectively destroys the small group of dopaminergic nerve cells in the substantia nigra of the brain which are also destroyed by degenerative processes in naturally occurring Parkinson's disease. There is even some discussion to the effect that idiopathic Parkinson's disease might be caused by MPTP or a similar chemical compound formed in the organism (Snyder, S. H., Nature 311, 514 (1984)). Possibly as a result of the specific metabolism of MPTP, the clinical features of the MPTP Parkinsonism syndrome have been thusfar only been detected in monkeys and man. The MPTP model produced in Rhesus monkeys is therefore exceptionally suitable for testing the effect of anti-Parkinson's drugs.

Seven Rhesus monkeys were given MPTP for three days at a daily dosage of 1×0.15 mg/kg by intramuscular route, then there was an interval of 3 days, then they were given the drug again for a further 3 days in a dosage of 1×0.30–0.40 mg/kg per day and showed the following symptoms: The animals were akinetic and incapable of taking water and food. They showed a typically bent posture; occasionally, cataleptic states occurred. The extremities showed rigor which was interspersed with clonic spasms during passive movement. Voluntary movements of the hindquarters and extremities could not generally be initiated even by extreme and painful stimulation.

After the intramuscular administration of B-HT 920 (50–100 mcg/kg) the first voluntary movements occurred at a time interval of 5 to 10 minutes, followed in the next 10 to 30 minutes by a gradual, extensive normalization of motor function. The animals were capable of taking food. They maintained thier normal posture within their cages and also behaved normally in terms of vigilance and species-specific behavior. The residual symptoms recorded were an occasional, transient, slight resting tremor and a reduction in brute strength. There was no sedation. The blood supply to the skin appeared to be increased compared with the state before the B-HT 920 was administered.

The effect of B-HT 920 diminished after about 3 hours and the animals reverted to the Parkinson's symptoms described above; fresh administration of B-HT 920 again resulted in an improvement or substantial removal of the clinical pathological symptoms. The advantageous effect of B-HT 920 was thus reproduced several times in each single animal.

No side effects were discovered at the dosages used.

The use of compound A and the acid addition salts thereof has the advantage over the thusfar conventional DA agonists that this substance will only act on the denervated post-synaptic DA receptors in the brain, so that in Parkinson patients the pharmacological (motor) effect of B-HT 920 would be restricted primarily to those DA systems of the brain which are affected by the disease. In other words:

Compound A and the acid addition salts thereof have a particularly powerful effect in *severe Parkinson cases* (high degree of denervation of the striatum DA receptors).

Furthermore, compound A and the physiologically acceptable acid addition salts thereof are well tolerated; for example, the oral LD$_{50}$ in the mouse is 455 mg/kg.

EXAMPLE I

Tablet core

| Composition: 1 Tablet core contains: | |
|---|---|
| B-HT 920 | 50 mcg |
| Lactose | 38.45 mg |
| Corn starch | 10.00 mg |
| Gelatine | 1.00 mg |
| Magnesium stearate | 0.50 mg |
| | 50.00 mg |

Method of preparation

A mixture of the active substance with lactose and corn starch is granulated with a 10% aqueous gelatine solution through a 1 mm screen, dried at 40° C. and passed through the same screen again. The granulate thus obtained is mixed with magnesium stearate and compressed to form tablet cores. The operation must be carried out in a darkened room.

Weight of core: 50 mg
Die: 5 mm, convex

The tablet cores thus obtained are coated in known manner with a coating consisting essentially of sugar and talc. The finished coated tablets are polished with bees wax.

Weight of coated tablet: 100 mg

EXAMPLE II

Suppositories

| 1 Suppository contains: | |
|---|---|
| B-HT 920 | 100.0 mcg |
| Suppository mass (e.g. Witepsol W 45) | 1690.0 mg |

Method of preparation

The finely powdered substance is stirred into the molten suppository mass, which has been cooled to 40° C., with an immersion homogenizer. At 35° C. the mass is poured into slightly chilled moulds.

EXAMPLE III

Ampoules containing 200 mcg of B-HT 920

| 1 Ampoule contains: | |
|---|---|
| B-HT 920 | 200.0 mcg |
| Citric acid | 7.0 mg |
| sec. sodium phosphate.2 H$_2$O | 3.0 mg |
| sodium pyrosulfite | 1.0 mg |
| Distilled water ad. | 1.0 ml |

Method of preparation:

The buffer substances, active substance and sodium pyrosulfite are dissolved successively in decocted water which has been cooled under a current of CO$_2$. The solution is made up to the specified volume with decocted water and filtered free from pyrogens.

Packaging: in brown ampoules under protective gas
Sterilisation: 20 minutes at 120° C.

The preparation and packaging of the ampoule solution must be carried out in a darkened room.

EXAMPLE IV

Coated tablets containing 0.1 mg of B-HT 920

| 1 tablet core contains: | |
|---|---|
| B-HT 920 | 100.0 mcg |
| Lactose | 36.0 mg |
| Corn starch | 12.4 mg |
| Gelatine | 1.0 mg |
| Magnesium stearate | 0.5 mg |
| | 50.0 mg |

Method of preparation:
Analogously to Example I.
Weight of core: 50 mg
Die: 5 mm, convex
Weight of coated tablet: 100 mg

EXAMPLE V

Coated tablets containing 0.2 mg of B-HT 920

| 1 tablet core contains: | |
|---|---|
| B-HT 920 | 0.2 mg |
| Digoxin | 0.25 mg |
| Lactose | 66.55 mg |
| Potato starch | 25.0 mg |
| Polyvinyl pyrrolidone | 2.0 mg |
| Magnesium stearate | 1.0 mg |
| | 95.0 mg |

Method of preparation:

A thorough mixture of the active substances with lactose and potato starch is granulated with a 10% solution of the polyvinyl pyrrolidone in ethanol through a 1.5 mm screen, then dried at 40° C. and passed through a 1.0 mm screen. The granulate thus obtained is mixed with magnesium stearate and compressed to form tablet cores.

Weight of core: 95.0 mg

Punch: 7 mm, convex

The tablet cores thus produced are coated in known manner with a coating consisting essentially of sugar and talc. The finished coated tablets are polished with beeswax.

Weight of coated tablet: 175 mg.

EXAMPLE VI

Gelatine capsules containing 300 mcg of B-HT 920

| 1 Capsule contains: | |
|---|---|
| B-HT 920 | 0.3 mg |
| Codeine phosphate | 10.0 mg |
| tartaric acid | 3.0 mg |
| Corn starch | 86.7 mg |
| | 100.0 mg |

Method of preparation:

The substances are intensively mixed and packed into opaque capsules of suitable size.

Capsule content: 100 mg.

We claim:

1. A method of treating Parkinson's disease or Parkinsonism, which comprises administering to a patient in need of such treatment a quantity of 2-amino-6-allyl-5,6,7,8-tetrahydro-4H-thiazolo[4,5-d]azepine, or a pharmaceutically acceptable acid addition salt thereof, sufficient to alleviate or remove the Parkinson's symptoms.

* * * * *